(12) United States Patent
Corne et al.

(10) Patent No.: US 10,457,563 B2
(45) Date of Patent: Oct. 29, 2019

(54) HIGHLY AMINATED SELF-ASSEMBLING FUNCTIONALIZED MESOPOROUS SILICA NANOPARTICLES AND METHOD OF SYNTHESIS

(71) Applicant: Luxembourg Institute Of Science And Technology (LIST), Esch/Alzette (LU)

(72) Inventors: Gaelle Corne, Audun-le-Tiche (FR); Damien Lenoble, Wellin (BE); Jean-Sebastien Thomann, Gorcy (FR)

(73) Assignee: Luxembourg Institute of Science & Technology (LIST), Luxembourg (LU)

( * ) Notice: Subject to any disclaimer, the term of this patent is extended or adjusted under 35 U.S.C. 154(b) by 0 days.

(21) Appl. No.: 15/746,298

(22) PCT Filed: Jul. 20, 2016

(86) PCT No.: PCT/EP2016/067327
§ 371 (c)(1),
(2) Date: Jan. 19, 2018

(87) PCT Pub. No.: WO2017/013182
PCT Pub. Date: Jan. 26, 2017

(65) Prior Publication Data
US 2018/0222754 A1    Aug. 9, 2018

(30) Foreign Application Priority Data

Jul. 22, 2015    (LU) .......................................... 92783

(51) Int. Cl.
*C01B 33/193*    (2006.01)
*C01B 37/02*    (2006.01)
(Continued)

(52) U.S. Cl.
CPC ............. *C01B 33/193* (2013.01); *C01B 37/02* (2013.01); *B82Y 5/00* (2013.01); *B82Y 40/00* (2013.01);
(Continued)

(58) Field of Classification Search
CPC ........... B82Y 30/00; B82Y 40/00; B82Y 5/00; C01B 37/02; C01P 2004/64; C01P 2006/16
See application file for complete search history.

(56) References Cited

U.S. PATENT DOCUMENTS

| 5,200,058 A | 4/1993 | Beck et al. |
| 2006/0079606 A1 | 4/2006 | Min et al. |

(Continued)

FOREIGN PATENT DOCUMENTS

| EP | 1890965 A1 | 2/2008 |
| GB | 2507983 A | 5/2014 |

OTHER PUBLICATIONS

Zhang, Xueao, et al. "Evaporation-Induced Self-Assembly of Amino-Functionalized Mesoporous Silica Thin Films by Sol-Gel Process." Journal of the American Ceramic Society 90.3 (2007): 965-968.*

(Continued)

*Primary Examiner* — Richard M Rump
(74) *Attorney, Agent, or Firm* — Sandberg Phoenix & von Gontard P.C.

(57) ABSTRACT

A method for self-assembling a mesoporous silica nanoparticle. The method comprises the step of condensing a silica precursor, a surfactant and a condensation agent in a solvent. Then, the addition of an organotriethoxysilane is performed. Finally, there is the step of removing the surfactant. The method is remarkable in that the portion of the organotriethoxysilane to the silica precursor is comprised between 5% and 15%. Additionally, a self-assembled mesoporous (Continued)

Figure 1:
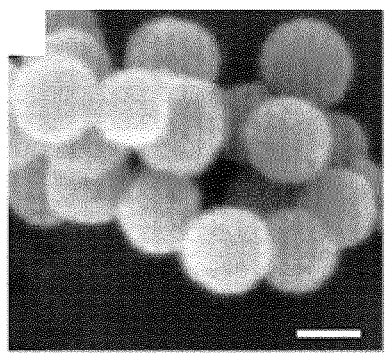

silica nanoparticle comprising at least one silica precursor and an organotriethoxysilane.

16 Claims, 6 Drawing Sheets

(51) Int. Cl.
    *B82Y 5/00* (2011.01)
    *B82Y 40/00* (2011.01)
(52) U.S. Cl.
    CPC ...... *C01P 2004/64* (2013.01); *C01P 2006/16* (2013.01)

(56) References Cited

U.S. PATENT DOCUMENTS

| | | |
|---|---|---|
| 2008/0175783 A1 | 7/2008 | Park et al. |
| 2010/0254890 A1 | 10/2010 | Yang et al. |
| 2014/0079774 A1 | 3/2014 | Brinker et al. |

OTHER PUBLICATIONS

Moeller, Karin, Johannes Kobler, and Thomas Bein. "Colloidal suspensions of nanometer-sized mesoporous silica." Advanced Functional Materials 17.4 (2007): 605-612.*
Cauda, Valentina, et al. "Multiple core-shell functionalized colloidal mesoporous silica nanoparticles." Journal of the American Chemical Society 131.32 (2009): 11361-11370.*
Urata, Chihiro, et al. "Dialysis process for the removal of surfactants to form colloidal mesoporous silica nanoparticles." Chemical Communications 34 (2009): 5094-5096.*
Ashley, Carlee E., et al. "Delivery of small interfering RNA by peptide-targeted mesoporous silica nanoparticle-supported lipid bilayers." Acs Nano 6.3 (2012): 2174-2188.*
Yoo, Hyojong, and Joonsung Pak. "Synthesis of highly fluorescent silica nanoparticles in a reverse microemulsion through double-layered doping of organic fluorophores." Journal of nanoparticle research 15.5 (2013): 1609.*
International Search Report for corresponding PCT/EP2016/067327 dated Sep. 28, 2016.
Selective Functionalization of the Outer and Inner Surfaces in Mesoporous Silica Nanoparticles, Johann Kecht, Axel Schlossbauer, and Thomas Bein, Chem. Mater. 2008, 20, 7207-7214.

* cited by examiner

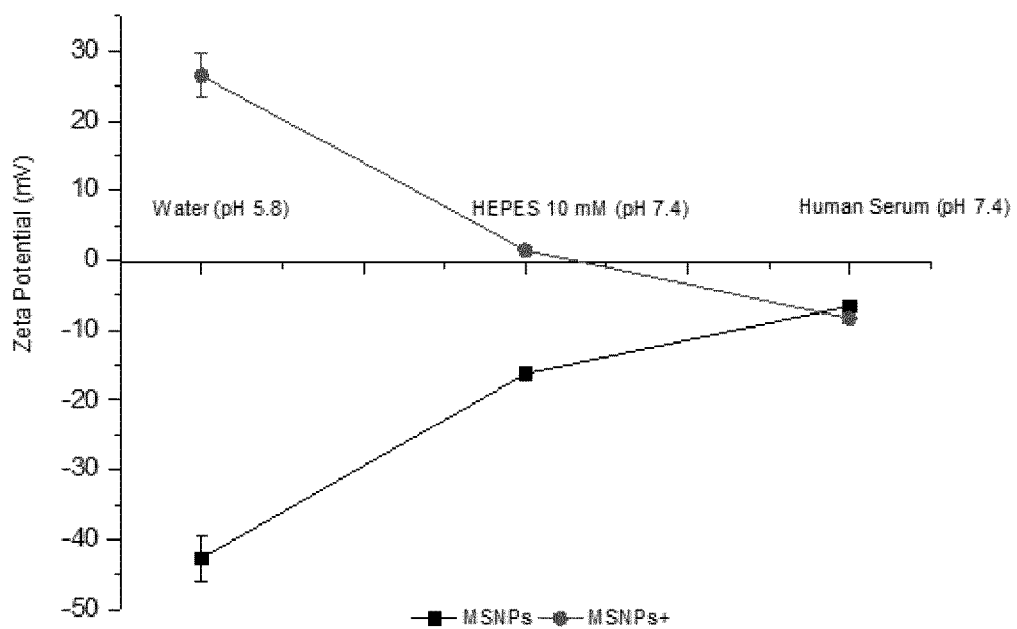
Fig. 17
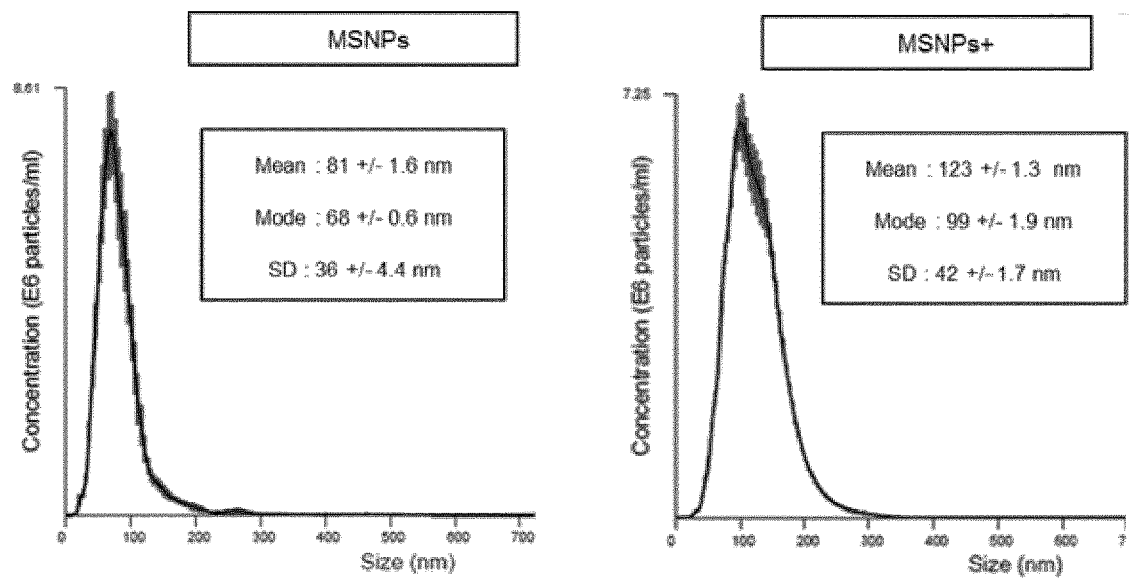
Fig. 18
Fig. 19

HIGHLY AMINATED SELF-ASSEMBLING FUNCTIONALIZED MESOPOROUS SILICA NANOPARTICLES AND METHOD OF SYNTHESIS

CROSS-REFERENCE TO RELATED APPLICATIONS

The present invention is the US national stage under 35 U.S.C. § 371 of International Application No. PCT/EP2016/067327, which was filed on Jul. 20, 2016, and which claims the priority of application LU 92783 filed on Jul. 22, 2015, the content of which (text, drawings and claims) are incorporated here by reference in its entirety.

FIELD

The invention is directed to the field of synthesis of mesoporous silica nanomaterials adapted to be used as nanovector for the encapsulation and the delivery of materials.

BACKGROUND

Mesoporous silica nanomaterials allow different biomedical applications such as drug delivery, therapeutic imaging, and diagnosis. In this context, mesoporous silica nanoparticles (MSNPs) have been hugely studied as a vector for drug delivery applications.

Mesoporous silica micro or nanoparticles are generally synthesized using template-assisted sol-gel methods.

In order to attach different structure around those MSNPs, such as, for example, a supported lipid bilayer (SLB), it is interesting to be able to functionalize the MSNPs with a reactive moiety which is on the external surface of the MSNPs, allowing subsequently further functionalization.

Among different methods, Bein and co-workers (*Chem. Mater.*, 2008, 20, 7207-7214) have reported the self-assembly of MSNPs, in particular functionalized MSNPs. The self-assembly is provided by mixing a surfactant, which is employed as structure-directing agent, a silica precursor, and an organotriethoxysilane, which will provide the functional moiety onto the external surface of the nanoparticles, in an alkaline aqueous media containing a polyalcohol, which is going to slow down the condensation rate of the silica species.

The surfactant is cetyltrimethylammonium chloride (CTACl).

The silica precursor is tetraethylorthosilicate (TEOS).

The organotriethoxysilane is 3-aminopropyltriethoxysilane (APTES). It can also be, for example, phenyltriethoxysilane (PTES).

The polyalcohol is triethanolamine (TEA).

The protocol provided by the Bein's research group requires the co-condensation of all of the above mentioned reagents to provide the self-assembly of the functionalized MSNPs.

Thus, a first mixture of TEOS, CTACl, TEA in water is prepared and is co-condensed with a mixture of TEOS and the organotriethoxysilane. The second mixture, comprising TEOS and the organotriethoxysilane, always contained 185 µmol of silane, namely 2% of the total amount of silane involved in the preparation of the MSNPs.

The second mixture can be added onto the first mixture at different time, depending of the nanoparticle growth.

By using this above co-condensation principle and such ratio, non-aggregated functionalized MSNPs were obtained.

However, the yield of functionalized, namely the yield of organotriethoxysilane incorporated within the external surface of the nanoparticles is dependent of the starting concentration of organotriethoxysilane, which is always below 2% of the total amount of silane involved in the preparation of the MSNPs.

The yield of the functionalization of the nanoparticles with the amino group (using subsequently APTES as organotriethoxysilane) was reported using ζ-potential measurements.

ζ-potential experiments performed after 10 or 30 minutes of particle growth at a pH of 6 indicates a ζ-potential between 0 mV and 5 mV. At more acidic pH values, the ζ-potential logically increases (up to 10 mV at a pH of 4 and up to more than 25 mV at a pH of 2 after 30 minutes of particle growth).

When the co-condensation route was not performed, namely when the organotriethoxysilane (at a concentration equal to 2% of the total amount of silane involved in the preparation of the MSNPs) was added directly (without condensation with TEOS), the final nanoparticles obtained where either aggregated (in the case where APTES was used) or non-functionalized (in the case where PTES was used).

Those results suggest that when the organotriethoxysilane is used at this concentration, the pores and the channels of the nanoparticles in formation becomes blocked. However, when co-condensation is previously performed, the organotriethoxysilanes are hydrolysed forming oligosilicate anions which can subsequently reacts with the silica wall which is built during the nanoparticle growth.

SUMMARY

The invention has for technical problem to provide a synthesis of non-aggregated functionalized MSNPs with an enhanced yield of incorporation of the functional group. The main objective is to provide more functional groups onto the external surface of the MSNPs in order to be able to anchor a SLB with more stability by preserving the fact that those functionalized MSNPs are non-aggregated.

The invention is directed to a method for self-assembling a mesoporous silica nanoparticle. The method comprises the step of condensing a silica precursor, a surfactant and a condensation agent in a solvent. Then, the addition of an organotriethoxysilane is performed. Finally, there is the step of removing the surfactant. The method is remarkable in that the portion of the organotriethoxysilane to the silica precursor is comprised between 5% and 15%.

According to various embodiments of the present invention, the portion of the organotriethoxysilane to the silica precursor is comprised between 6% and 14%, in various instances between 7% and 13%, for example between 8% and 12%, e.g., between 9% and 11%.

In various embodiments, the portion of the organotriethoxysilane to the silica precursor is 10%.

In various embodiments, the silica precursor is tetraethyl orthosilicate, the surfactant is cetyltrimethylammonium chloride, the condensation agent is triethanolamine and/or the organotriethoxysilane is (3-aminoproplyl)triethoxysilane.

In various embodiments, the number of equivalents of the condensation agent relative to one equivalent of the silica precursor is comprised between 1.6 and 2.4, in various instances between 1.7 and 2.3, for example between 1.8 and 2.2, e.g., between 1.9 and 2.1.

In various embodiments, the number of equivalents of the condensation agent relative to one equivalent of the silica precursor is 2.0.

In various embodiments, the number of equivalents of the surfactant relative to one equivalent of the silica precursor is comprised between 0.22 and 0.30, in various instances between 0.23 and 0.29, for example between 0.24 and 0.28, e.g., between 0.25 and 0.27.

In various embodiments, the number of equivalents of the surfactant relative to one equivalent of the silica precursor is 0.26.

In various embodiments, the organotriethoxysilane is added between 10 minutes and 30 minutes, in various instances between 15 minutes and 25 minutes, for example at 20 minutes.

In various embodiments, the step of removing the surfactant is a combination of a dialysis process and an extraction in hydrochloric acid.

In various embodiments, the dialysis process is repeated five times.

In various embodiments, the solvent is a mixture of milliQ water and ethanol.

In various embodiments, the number of equivalents of milliQ water relative to one equivalent of the silica precursor is comprised between 100 and 134 or between 217 and 251, in various instances between 105 and 129 or between 222 and 246, for example between 110 and 124 or between 227 and 241, e.g., between 116 and 118 or between 233 and 235.

In various embodiments, the number of equivalents of milliQ water relative to one equivalent of the silica precursor is 117.35 or 234.7.

In various embodiments, the number of equivalents of ethanol relative to one equivalent of the silica precursor is comprised between 2 and 8 or between 9 and 14, in various instances between 3 and 7 or between 10 and 13, for example between 4 and 6 or between 11 and 12.

In various embodiments, the number of equivalents of ethanol relative to one equivalent of the silica precursor is 5.88 or 11.76.

In various embodiments, the mesoporous silica nanoparticle is adapted for being incorporated within a supported lipid bilayer.

The invention is further directed to a self-assembled mesoporous silica nanoparticle. The self-assembled mesoporous silica nanoparticle comprises at least one silica precursor and at least one organotriethoxysilane. The mesoporous silica nanoparticle is remarkable in that the portion of the organotriethoxysilane to the silica precursor is comprised between 5% and 15%.

In various embodiments, the portion of the organotriethoxysilane to the silica precursor is comprised between 6% and 14%, in various instances between 7% and 13%, for example between 8% and 12%, e.g., between 9% and 11%.

In various embodiments, the portion of the organotriethoxysilane to the silica precursor is 10%.

In various embodiments, the silica precursor is tetraethyl orthosilicate and/or the organotriethoxysilane is (3-aminopropyl)triethoxysilane.

In various embodiments, the self-assembled mesoporous silica nanoparticle is incorporated within a supported lipid bilayer.

The invention is particularly interesting in that it allows the synthesis of functionalized mesoporous silica nanoparticles which are non-aggregated and with a high level of functionalization on the external surface of the nanoparticles. These types of highly stable nanoparticles are suitable for being incorporated within a negatively charged supported lipid bilayer and therefore are further suitable for encapsulating an object (such as a drug, an active moiety . . . ). Biomedical applications such as drug delivery, therapeutic imaging and diagnosis can be envisioned.

DRAWINGS

FIG. 1 exemplarily illustrates a SEM (Scanning Electron Microscope) picture of MSNPs, with a size of 53±6 nm (50 counts, scale bar=50 nm).

Figure 2:
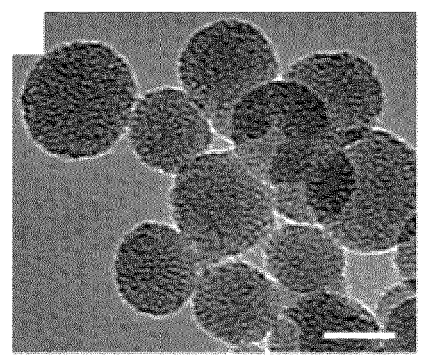

FIG. 2 exemplarily illustrates a TEM (Transmission Electron Microscope) picture of MSNPs, with a size of 53±6 nm (scale bar=50 nm).

Figure 3:
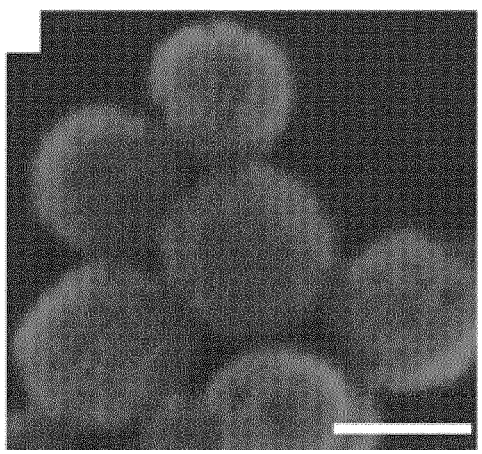

FIG. 3 exemplarily illustrates a SEM picture of MSNPs, with a size of 35±6 nm (50 counts, scale bar=35 nm).

Figure 4:
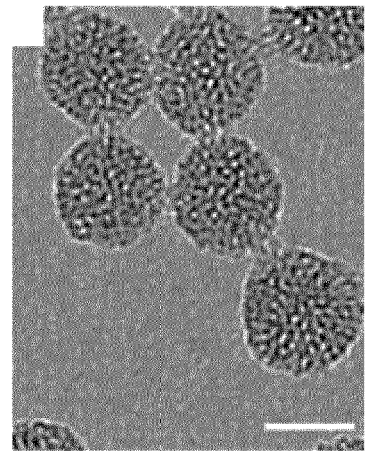

FIG. 4 exemplarily illustrates a TEM picture of MSNPs, with a size of 35±6 nm (scale bar=35 nm).

Figure 5:
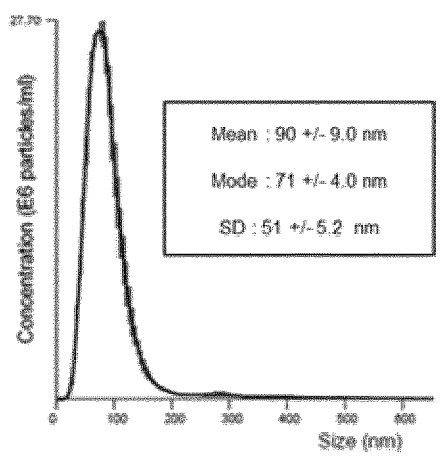

FIG. 5 exemplarily illustrates NTA (Nano Tracking Analysis) of MSNPs, with a size of 35±6 nm.

Figure 6:
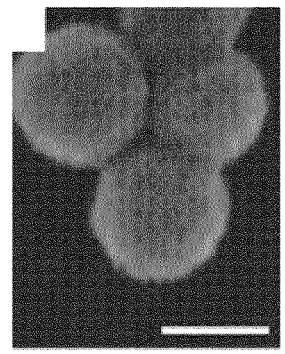

FIG. 6 exemplarily illustrates a SEM picture of MSNPs+, with a size of 50.9±3.6 nm (50 counts, scale bar=50 nm).

Figure 7:
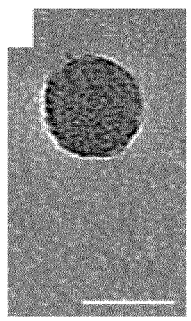

FIG. 7 exemplarily illustrates a TEM picture of MSNPs+, with a size of 50.9±3.6 nm (scale bar=50 nm).

Figure 8:
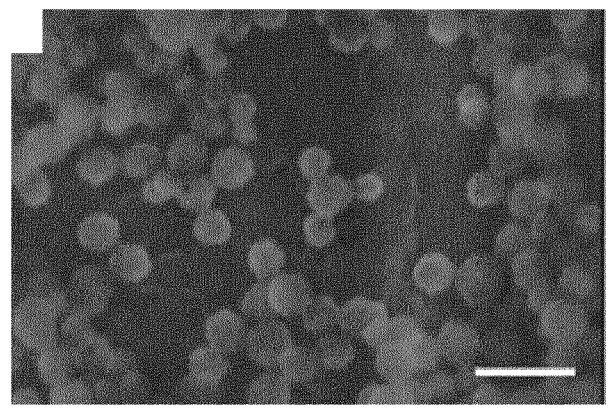

FIG. 8 exemplarily illustrates a SEM picture of MSNPs+, with a sized of 36.5±5 nm (50 counts, scale bar=100 nm).

Figure 9:
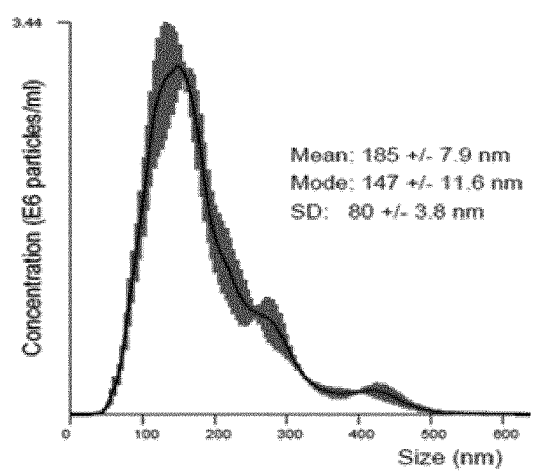

FIG. 9 exemplarily illustrates NTA analysis of MSNPs+, with a sized of 36.5±5 nm.

Figure 10:
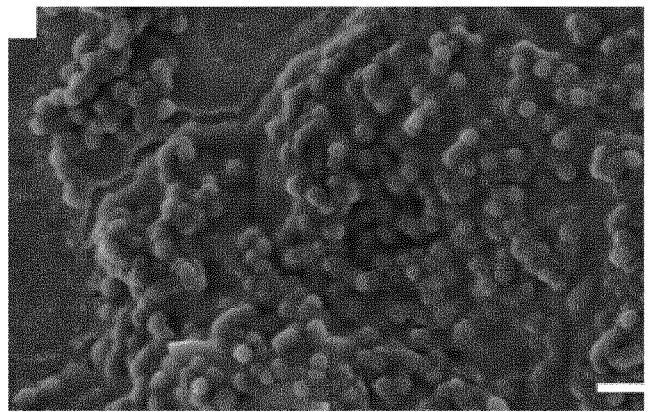

FIG. 10 exemplarily illustrates a SEM picture of purification in ammonium nitrate extraction of MSNPs showing the presence of CTACl template and the aggregation between the nanoparticles (scale bar=200 nm).

Figure 11:
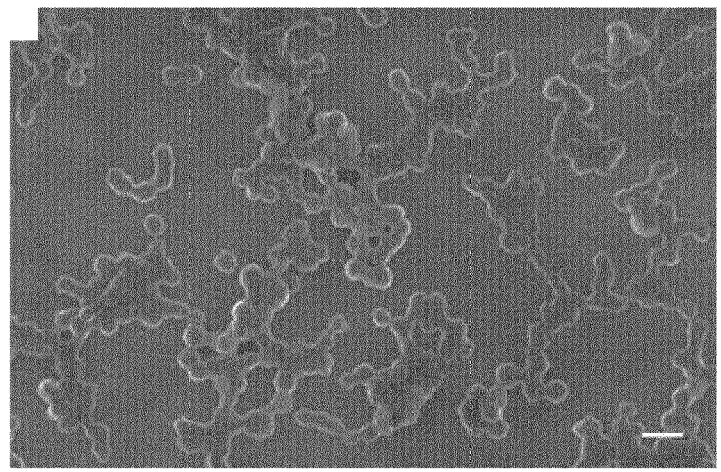

FIG. 11 exemplarily illustrates a SEM picture of MSNPs after the acid dialysis process (scale bar=200 nm).

Figure 12:
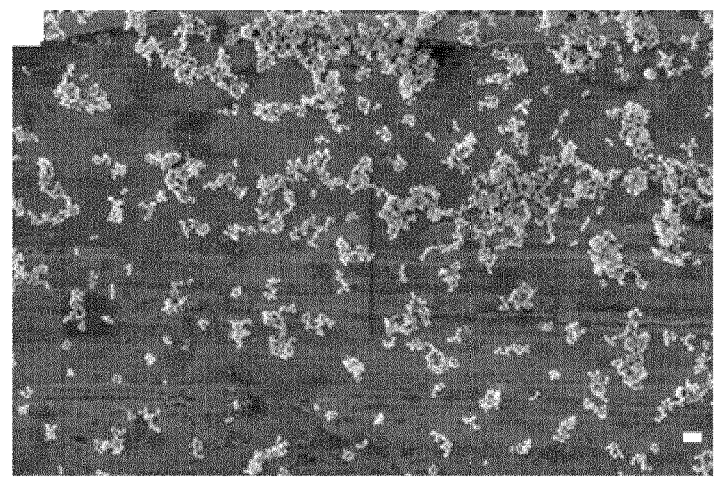

FIG. 12 exemplarily illustrates a SEM picture of the MSNPs dispersed in water after total extraction (scale bar=200 nm).

Figure 13:
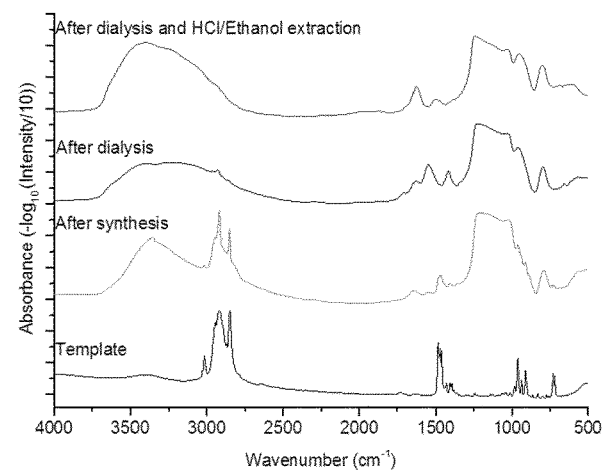

FIG. 13 exemplarily illustrates a Diffuse-Reflectance IR Fourier Transform (DRIFT) spectrum of MSNPs+ before and after acid dialysis process, and after total extraction of the template via ultrasound in acid solution.

Figure 14:
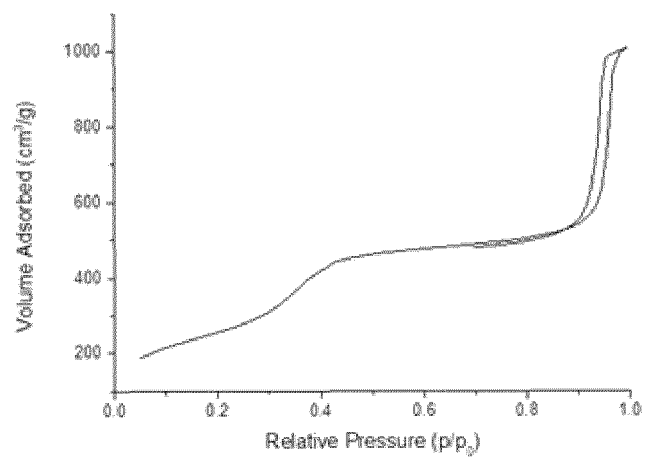

FIG. 14 exemplarily illustrates Nitrogen adsorption of MSNPs, used for Barrett-Joyner-Halenda model determination.

Figure 15:
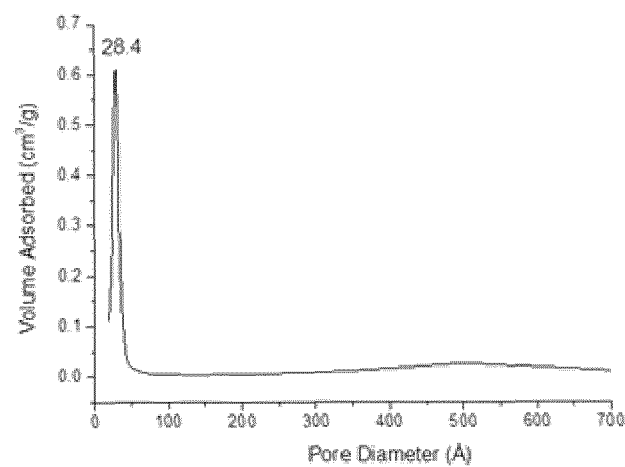

FIG. 15 exemplarily illustrates pore size distribution in volume of MSNPs.

Figure 16:
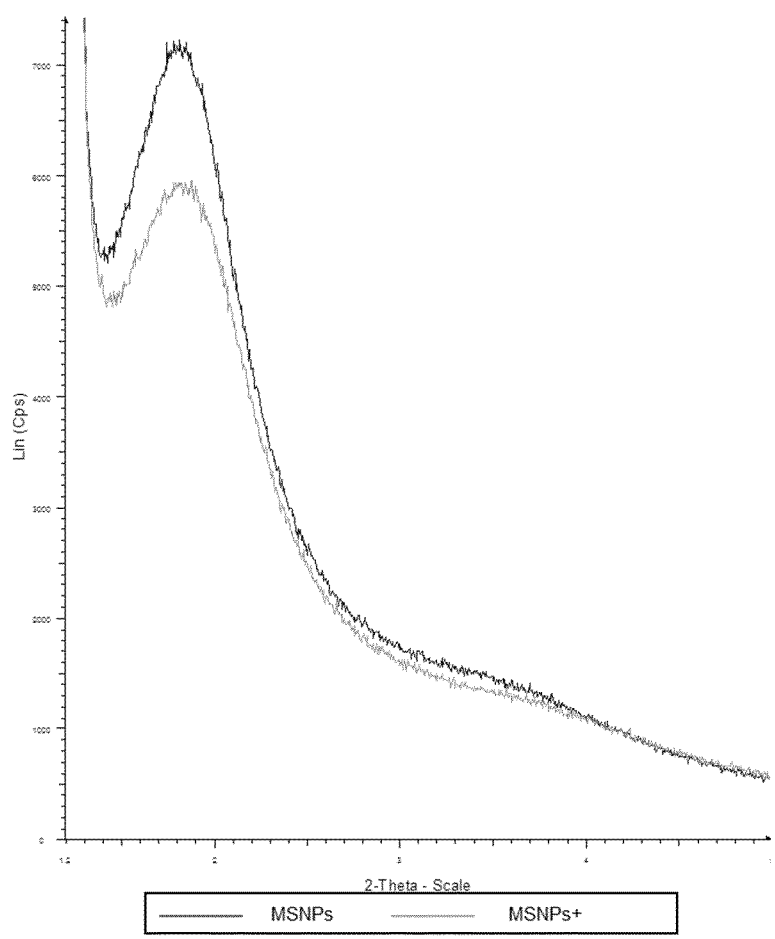

FIG. 16 exemplarily illustrates XRD patterns of MSNPs and MSNPs+ after total extraction.

FIG. 17 exemplarily illustrates a ζ-potential table for MSNPs and MSNPs+ performed on a Malvern Instruments in water (pH 5.5). Data are mean±SE and represent three independent experiments.

FIG. 18 exemplarily illustrates NTA analysis of MSNPs in milliQ water.

FIG. 19 exemplarily illustrates NTA analysis of MSNPs+ in milliQ water.

DETAILED DESCRIPTION

The self-assembling of the mesoporous structure was provided by a radial growth using tetraethyl orthosilicate (TEOS) as silica precursor, the surfactant cetyltrimethylammonium chloride solution (CTACl) as a pore template, and triethanolamine (TEA) as condensation agent.

This synthesis formed non-aggregated MSNPs with a dry size of about 54 nm as shown by TEM and SEM pictures (FIGS. 1 and 2).

Smaller MSNPs have potential interest in the perspective to cross biological barriers such as the blood brain barrier. For this purpose, the size of MSNPs was decreased by diluting by two the reagents to get particles of a size around 35 nm. Decreasing concentrations of reactants slows down the condensation of the silica nuclei which can explain the smaller size of these MSNPs (FIGS. 3 and 4).

A minor but still significant intra-particular aggregation of MSNPs 35 nm was observed during hydrodynamic size studies by using Nano Tracking Analysis (NTA) (FIG. 5). Due to their smaller size, MSNPs of 35 nm tend to aggregate more in water than those of 55 nm.

Functionalization of MSNPs with amino moieties provides positively charged nanoparticles. Those positively charged nanoparticles (MSNPs+) will be used to be incorporated into negatively charged structures, such as negatively charged supported lipid bilayer.

A high density of amino moieties is expected to reinforce electrostatic interaction between the negatively charged supported lipid bilayer and the MSNPs+. To achieve such an amino coating, (3-aminopropyl)triethoxysilane (APTES) were added 20 minutes after the beginning of the MSNPs 55 and 35 nm synthesis. Due to the presence of the template CTACl which cloaks the pores, this process allows to functionalize the outer nanoparticle surface prior to the inner surface. However, a functionalization of the inner surface cannot be excluded due to the diffusion of APTES inside the nanoparticle.

The size of MSNPs+ (55 nm) has been visualized by SEM and TEM analysis (FIGS. 6 and 7).

A minor increase of size is observed compared to non-functionalized MSNPs. A similar amino coating process was developed for MSNPs of 35 nm. SEM characterization of MSNPs+ (35 nm) is shown in FIG. 8. The dry size of these particles does not significantly changes compared to the non-functionalized MSNPs of 35 nm. Nevertheless, in water, MSNPs+ (35 nm) tends to aggregate more than MSNPs (35 nm) as shown by the NTA analysis depicted in FIG. 9.

In order to remove the template inside MSNPs+ and MSNPs, several extraction methods were tested. Template extraction based on acidic conditions and ionic competition was described to decrease particle aggregation compared to the template calcination. Some methods based either on ethanol/HCl extraction, acid dialysis or ammonium nitrate extraction were already published.

Nevertheless, applying these approaches on our NPs failed to completely remove the template as shown by the SEM analysis (FIGS. 10 and 11).

Successful combination of acid dialysis and extraction in ethanol/HCl was highly efficient as demonstrated on FIG. 12 depicting a SEM picture of the MSNPs dispersed in water after total extraction.

Fourier Transform Infrared Spectroscopy (FTIR) performed on MSNPs+ (55 nm) samples confirmed these observations (FIG. 13). The C—H stretching vibration between 2830-2970 $cm^{-1}$ and the C—H bending vibration 1470 $cm^{-1}$ of the CTACl template had disappeared after the total MSNPs+ extraction. Once the template is removed, the water bending peak at 1630 $cm^{-1}$ increased due to the presence of hydrophilic silanol functions on the surface of MSNPs+. The possibility to remove the residual surfactant demonstrates that the pores of MSNPs+ are not cloaked by the APTES functionalization. In addition, SEM and TEM pictures of MSNPs+ showed a clear porosity of these structures (FIGS. 6 and 7).

Specific surface and pore sizes of MSNPs were determined by Brunauer, Emmett and Teller (BET) measurements. The Barrett-Joyner-Halenda model calculated a high surface area of 935.5 $m^2/g$ (FIG. 14), and pores size distribution of about 2.8 nm (FIG. 15).

X-ray Diffraction (XRD) analyses were performed to acquire crystallography insights of the NPs structure. The broad peak depicted in FIG. 16 is centered on 1.9° and can be attributed to the wormlike structure. The pore size calculated using the Bragg equation, is about 2.9 nm which is similar to the values calculated from the BET theory.

The ζ-potential of MSNPs and MSNPs+ were investigated in different media: milliQ water, and HEPES buffer (FIG. 17). These measurements have been made without performing any filtration or size exclusion prior to analysis. The size has been measured using NTA whereas ζ-potential has been measured by using Malvern Nano Zetasizer®. In milliQ water, at a pH value of 5.8, MSNPs+ have a charge of +26.47 mV. In comparison with the results obtained by the Bein's research group, for a similar value of pH, the ζ-potential of the MSNPs+ of the present invention is significatively higher. Indeed, at a pH value of 6.0, the ζ-potential of the Bein's nanoparticle is comprised between 0 mV and 5 mV. This is a clear indication that the functionalization of the MSNPs by the organotriethoxysilane, i.e. (3-aminopropyl)triethoxysilane (APTES), resulting in MSNPs+, namely in nanoparticles bearing a reactive organic group at its external surface, proceeds in a more efficacious manner when the protocol according to present invention is followed.

A further result (not shown) indicates that at a pH value of 4.0, the ζ-potential measurement demonstrates a charge of +37 mV onto the MSNPs+. The size of MSNPs+ in water is about 99 nm (FIG. 19) whereas the size of MSNPs in water is about 68 nm (FIG. 18).

Experimental Section

Nanoparticles Synthesis

Chemical Materials

Cetyltrimethylammonium chloride (CTACl), TEA: Triethanolamine, tetraorthosilicate (TEOS), (3-aminopropyl)triethoxysilane (APTES) were purchased from Sigma-Aldrich Co. Ammonium acetate and Methanol were purchased from Biosolve.

Synthesis of 55 nm Mesoporous Silica Nanoparticles (MSNPs 55 mn)

A stock solution was prepared by mixing 13.75 mL (762.8 mmol) of milliQ water, 2.23 mL (38.2 mmol) of absolute ethanol, and 2.23 mL (1.69 mmol) of 25% CTACl by stirring in Radleys Tech® carrousel for 10 minutes under argon atmosphere. Then, TEA (1.78 mL; 13.37 mmol) was added and mixed with stock solution until complete dissolution. Stock solution was heated at 60° C., and then TEOS (1.454 mL; 6.5 mmol) was added in drops over 2-3 minutes. The reaction was stirred for 2 hours, under argon atmosphere. The molar ratio of this reaction is: TEOS/CTACl/TEA/$H_2O$/EtOH 1/0.26/2/117.35/5.88.

The mesoporous silica nanoparticles which are formed display a wormhole-type matrix.

Synthesis of 35 nm Mesoporous Silica Nanoparticles (MSNPs 35 nm)

During this reaction, the reagent mixture was diluted by two. Stock solution was prepared by mixing 27.5 mL (1.52 mol) of milliQ water, 4.46 mL (76.4 mmol) of absolute ethanol, and 2.23 mL (1.69 mmol) of 25% CTACl in Radleys Tech® carrousel for 10 minutes under argon atmosphere. Then, the same synthesis process than the MSNPs 55 nm is applied with a molar ratio of: TEOS/CTACl/TEA/H$_2$O/EtOH 1/0.26/2/234.7/11.76.

The mesoporous silica nanoparticles which are formed display a wormhole-type matrix.

Synthesis of Mesoporous Silica Nanoparticles Positively Charged (MSNPs+)

After 20 minutes of MSNPs 55 nm reaction, 150 μL of APTES (0.64 mmol) were added inside the solution. The reaction was stirred for 2 hours, under argon atmosphere. The molar ratio of this reaction is: TEOS/CTACl/TEA/H2O/EtOH/APTES 1/0.26/2/117.35/5.88/0.1.

Template Extraction

The template extraction was performed by the combination of dialysis process and washing in hydrochloric acid. For the dialysis process, 50 mL of mesoporous silica nanoparticles were transferred into a dialysis membrane composed of cellulose (Molecular Weigh Cut Off=15 000 Da, Spectrum Labs)). Nanoparticles were washed during 24 h against 1 L of the mixture containing 3 M acetic acid, and ethanol (1:1) to remove CTACl from inside nanoparticle pores. This process was repeated five times. To remove the residual surfactant, the NPs were washed in HCl/Ethanol (25 mL conc.HCl in 100 mL EtOH) solution follow by 20 minutes centrifugation at 45 000 g by Beckman™ Allegra® 64R. The NPs were washed five times in the extraction solution for 2 hours under sonication. And, one last washing was performed in water.

Nanoparticles Characterization

XRD Analysis

The MSNPs and MSNPs+ samples were dried by lyophilization, to get 100 mg of powder. The silica nanomaterials were characterized by X-ray diffraction (XRD) in Brüker D8 Discover® HR XRD. The pore size was calculated by the Bragg's law: nλ=2d sin θ (1) With n the order of diffraction (n=1), λ the diffracted wavelength (i.e. copper X-Ray source, λCopper=1.54), d the grating space between atomic lattice planes, and θ the angle between the incident beam and the scattering planes.

BET Experiments

The MSNPs and MSNPs+ samples were evaporated by lyophilization, to get 100 mg of powder. The textural properties, including the BET (Brunauer-Emmett-Teller) specific surface area (SBET), specific pore volume (Vp) and pore diameter (Dp), were determined from low-temperature N$_2$ adsorption-desorption measurements collected using an ASAP 2010 Micrometrics apparatus. Prior to the analysis, the samples were degassed under vacuum at 150° C. until the static pressure was less than 6.6×10$^{-4}$ Pa. The specific surface area was calculated from the N$_2$ sorption isotherm using the BET equation and taking into account the cross-sectional area of a physically adsorbed N$_2$ molecule (0.1620 nm$^2$). The pore diameter and pore size distributions were calculated from the desorption branch of the isotherms using the Barrett-Joyner-Halenda (BJH) method.

DLS Analysis

Malvern Nano Zetasizer® measure the size and Zeta potential of NPs by using dynamic light scattering size (DLS). The analysis was performed with 0.1 mg/mL for each sample.

NTA Analysis

Nanoparticles Tracking Analysis (NTA) used a light scattering method which relates the rate of Brownian motion to particle size. This method allows direct and real time visualizing and analyzing of the NPs in liquids. During NTA measurement, NPs are illuminated by a focused laser beam and analyzed by the light scattered by each individual particle in the microscope onto the image sensor of a charge-coupled device (CCD) camera. The camera visualizes and records the frames of the particles in solution. The NTA software identifies and individually tracks the particles moving under Brownian motion. This measurement uses the temperature and the viscosity of the liquid to calculate particle size through the Stokes-Einstein equation. The Nanosight® analyses the particles with a size range from 30 to 1 μm. The samples were diluted at 0.01 mg/mL for analysis.

FT-IR Spectroscopy

Each sample was mixed with KBr in a weight ratio of 1.5:100. Samples were ground for 2 minutes and then pressed into a pellet under 450 kg·cm$^{-3}$. The spectra are performed with FTIR Brüker VERTEX 70 equipped with an MCT detector via an Attenuated Total Reflection (ATR), and KBr background is substracted.

Scanning Electron Microscopy (SEM) Analysis of Nanoparticles

One drop of each silica sample (MSNPs+ and MSNPs) was deposited on a copper support and dried for 3 hours. Pictures were acquired on a FEI HELIOS NanoLab 650™ scanning electron microscopy working at 2 kV.

Transmission Electron Microscopy (TEM) Analysis of Nanoparticles

To ensure the relevant dispersion of MSNPs, NanoPlus-Grids with a 15 nm Nitride monolayer were used as analysis support. One drop of each silica sample was deposited on a grid and fully dried before measurement. The shape, porosity and size of the nanoparticles were characterized by FEI Tecnaï™ Transmission Electronic Microscopy (TEM) operating at 200 kV.

The invention claimed is:

1. A method for self-assembling a mesoporous silica nanoparticle, said method comprising the following steps
    a) condensing a silica precursor, a surfactant and a condensation agent in a solvent;
    b) adding an organotriethoxysilane;
    c) removing said surfactant;
    wherein the portion of said organotriethoxysilane to said silica precursor is comprised between 5% and 15%.

2. The method according to claim 1, wherein the portion is 10%.

3. The method according to claim 1, wherein one of the silica precursor is tetraethyl orthosilicate, the surfactant is cetyltrimethylammonium chloride, the condensation agent is triethanolamine and the organotriethoxysilane is (3-aminoproplyl)triethoxysilane.

4. The method according to claim 1, wherein the number of equivalents of the condensation agent relative to one equivalent of the silica precursor is comprised between 1.6 and 2.4.

5. The method according to claim 1, wherein the number of equivalents of the condensation agent relative to one equivalent of the silica precursor is 2.0.

6. The method according to claim 1, wherein the number of equivalents of the surfactant relative to one equivalent of the silica precursor is comprised between 0.22 and 0.30.

7. The method according to claim 1, wherein the number of equivalents of the surfactant relative to one equivalent of the silica precursor is 0.26.

8. The method according to claim 1, wherein the organotriethoxysilane is added at a time between 10 minutes and 30 minutes after step a).

9. The method according to claim 1, wherein the step of removing the surfactant is a combination of a dialysis process and an extraction in hydrochloric acid.

10. The method according to claim 9, wherein the dialysis process is repeated five times.

11. The method according to claim 1, wherein the solvent is a mixture of milliQ water and ethanol.

12. The method according to claim 11, wherein the number of equivalents of milliQ water relative to one equivalent of the silica precursor is comprised one of between 100 and 134 and between 217 and 251.

13. The method according to claim 11, wherein the number of equivalents of milliQ water relative to one equivalent of the silica precursor is one of 117.35 and 234.7.

14. The method according to claim 11, wherein the number of equivalents of ethanol relative to one equivalent of the silica precursor is comprised one of between 2 and 8 and between 9 and 14.

15. The method according to claim 11, wherein the number of equivalents of ethanol relative to one equivalent of the silica precursor is one of 5.88 and 11.76.

16. The method according to claim 1, wherein the mesoporous silica nanoparticle is adapted for being incorporated within a supported lipid bilayer.

\* \* \* \* \*